US007056725B1

(12) United States Patent  (10) Patent No.: US 7,056,725 B1
Lu  (45) Date of Patent: Jun. 6, 2006

(54) VEGETABLE ALGA AND MICROBE PHOTOSYNTHETIC REACTION SYSTEM AND METHOD FOR THE SAME

(76) Inventor: Chao-Hui Lu, 7F, No. 1029, Ta Hsueh Rd., Hsin Chu City (TW)

( * ) Notice: Subject to any disclaimer, the term of this patent is extended or adjusted under 35 U.S.C. 154(b) by 0 days.

(21) Appl. No.: 11/019,166

(22) Filed: Dec. 23, 2004

(51) Int. Cl.
  *C12M 1/00* (2006.01)
(52) U.S. Cl. ............................... 435/292.1; 435/293.1; 435/293.2
(58) Field of Classification Search ............... 435/292.1
  See application file for complete search history.

(56) References Cited

U.S. PATENT DOCUMENTS 4,148,691 A * 4/1979 Malick ................. 435/293.1
4,868,123 A * 9/1989 Berson et al. ........... 435/286.6

FOREIGN PATENT DOCUMENTS

TW         95219504.6         9/1996

* cited by examiner

*Primary Examiner*—David Redding
(74) *Attorney, Agent, or Firm*—Rosenberg, Klein & Lee

(57) ABSTRACT

A vegetable alga and microbe photosynthetic reaction system and method for the same is used for vegetable algae and microbe cultivation liquid and algae seeds infused herein to circularly conduct photosynthesis and discharge oxygen; the vegetable alga and microbe photosynthetic reaction system comprises a photosynthetic reaction unit, a pressure liquid infusion unit, and an oxygen discharge and regulation unit; the photosynthetic reaction unit is a light permeable pipeline; the oxygen discharge and regulation unit is assembled with an oxygen discharge can, a liquid collection can, and a regulation can for facilitating production and assembly, and many oxygen discharge points so that oxygen formed in the cultivation liquid can be quickly evaporated.

14 Claims, 3 Drawing Sheets

VEGETABLE ALGA AND MICROBE PHOTOSYNTHETIC REACTION SYSTEM AND METHOD FOR THE SAME

BACKGROUND OF THE INVENTION

1. Field of the Invention

This invention relates to a photosynthetic reaction system and a method for the same and particularly relates to a vegetable alga and microbe photosynthetic reaction system and a method for the same.

2. Description of Related Art

Spirulina, a blue-green alga, is high in protein, minerals and fermenting organisms that are beneficial to human health. It is widely recommended as a part of a healthy diet. Through a photosynthetic reaction system, a cultivation liquid for spirulina can be added into the growing environment so that enough photosynthesis occurs to supply ample nutrients to the cells of the algae. Oxygen can then be evaporated from the cultivation liquid so that the spirulina may grow and multiply in large quantities.

A conventional photosynthetic reaction system for spirulina uses a large, open-air cultivation pond. The cultivation liquid for spirulina is contained in the cultivation pond to assist in achieving photosynthesis. However, the cultivation pond requires a large area, consumes lots of energy, and the photosynthetic reaction is often affected by the weather. Pollution also affects the outcome, decreasing the algae's quality. As such, the prior art method for producing the spirulina has many drawbacks for producers.

Another conventional photosynthetic reaction system for the spirulina is a photosynthetic reaction apparatus for spirulina described in Chinese Patent No. CN95219504.6. The apparatus is formed with a reaction tower and a vertical flat spiral piping of double rows. The reaction tower and piping are made of a material that is light permeable thus allowing photosynthesis to occur. A bulla plate and a cooling and heating exchanger are provided in the reaction tower to extract oxygen from the cultivation liquid and to control the temperature of the cultivation liquid. The photosynthetic reaction apparatus for spirulina exists mainly to provide a sealed recycling system for solutions to various problems occurring in conventional cultivation ponds. Industrialized mass production of the photosynthetic reaction for spirulina is not recommended because the reactor faces many problems such as a complicated production process, high costs, fragility, difficulties in extracting the oxygen, difficulties in controlling the temperature of the cultivation liquid, and difficulties in maintaining the cleanliness and functioning of the reaction tower so as to avoid affecting the photosynthetic reaction and impacting upon the quality of the algae.

Indeed, as can be understood from a reading of the description above, a further improvement is obviously required for the conventional photosynthetic reaction system for spirulina as it is obviously inconvenient and imperfect.

For this reason, in consideration of improving upon the defects described above, the inventor, having concentrated their studies and operating in coordination with academic theories, has finally provided this invention as a reasonable design and an effective improvement over the defects mentioned above.

SUMMARY OF THE INVENTION

This invention provides a vegetable alga and microbe photosynthetic reaction system and method for the same so that the system occupies less area, consumes less power, works without weather restrictions, and, especially, prevents the alga from being polluted whilst maintains a high quality of alga.

This invention secondly provides a vegetable alga and microbe photosynthetic reaction system and method for the same so that the oxygen formed in the cultivation liquid is quickly evaporated to maximize production efficiency and aid the process of industrialized mass production.

This invention further provides a vegetable alga and microbe photosynthetic reaction system and method for the same in which the production process and assembly of the necessary machinery are simple and the system is not easily damaged, thereby lowering costs.

This invention further provides a vegetable alga and microbe photosynthetic reaction system and method for the same wherein cleaning and maintenance of the machinery is simple, ensuring the photosynthetic effect and the quality of the alga.

This invention further provides a vegetable alga and microbe photosynthetic reaction system and method for the same that efficiently controls the temperature of the cultivation liquid.

In order to achieve the objectives mentioned above, this invention provides a vegetable alga and microbe photosynthetic reaction system comprising a photosynthetic reaction unit, a pressure liquid infusion unit, and an oxygen discharge and regulation unit. The photosynthetic reaction unit is a light permeable pipeline. An inlet of the pressure liquid infusion unit leads to an outlet of the light permeable pipeline. The oxygen discharge and regulation unit comprises a hollow oxygen injection and discharge device and a hollow liquid level regulation device, the oxygen injection and discharge device comprises an oxygen discharge can and a liquid collection can that are joined together, the oxygen discharge can is provided with a liquid entrance, a top exhaust, and a hollow pipe wall, the liquid entrance leads to an exit of the pressure liquid infusion unit, the top exhaust is located at a top of the oxygen discharge can, the hollow pipe wall extends from the top exhaust downwards and is correspondingly located at an inside of the liquid entrance, the liquid level regulation device comprises a regulation can leading to the liquid collection can, and an entrance of the light permeable pipeline leads to the regulation can.

Through connections between the photosynthetic reaction unit, the pressure liquid infusion unit, and the oxygen discharge and regulation unit, the vegetable algae and microbe cultivation liquid and algae seeds infused herein may circularly perform photosynthesis and discharge oxygen within multiple rows of straight sealed piping. Such an arrangement allows the system to occupy less area, consume less power, work irrespective of the weather, and prevent the alga from becoming polluted, thereby ensuring its quality. Through the arrangement of the liquid entrance, the top exhaust and the hollow pipe wall, any oxygen that forms in the cultivation liquid is quickly evaporated thus maximizing production efficiency. Through the assembly of the oxygen discharge can and the liquid collection can into the hollow oxygen injection and discharge device, production and assembly procedures are simple and the system is not easily damaged, thereby lowering costs. Through the assembly of the oxygen discharge can and the liquid collection can and the design of the light permeable pipeline, cleaning and maintenance are also simple, ensuring the photosynthetic reaction takes place effectively, thus ensuring the quality of the alga.

Furthermore, the oxygen injection and discharge device comprises an exhaust pipe connected to the oxygen discharge can, a middle section of the oxygen discharge can is provided with a necking portion and a side exhaust in which the side exhaust is located below the necking portion, a top end of the exhaust pipe pierces through the hollow pipe wall, and a bottom end of the exhaust pipe is formed with an expansion portion and is correspondingly located at an inner side of the side exhaust. The oxygen that forms in the cultivation liquid thereby may be quickly evaporated.

Moreover, the vegetable alga and microbe photosynthetic reaction system according to this invention comprises a heating unit connected between the exit of the light permeable pipeline and the entrance of the pressure liquid infusion unit.

Furthermore, the vegetable alga and microbe photosynthetic reaction system according to this invention comprises a sprinkling unit located above the photosynthetic reaction unit.

Through this abovementioned arrangement of the heating unit and the sprinkling unit, the temperature of the cultivation liquid may be efficiently controlled.

This invention provides a method for the vegetable alga and microbe photosynthetic reaction, comprising:
(1) providing a light permeable pipeline, a pressure liquid infusion unit, and an oxygen discharge and regulation unit;
(2) injecting a cultivation liquid and algae seeds into the light permeable pipeline, the cultivation liquid flows into the light permeable pipeline to generate a photosynthetic reaction which further generates oxygen, the cultivation liquid then flows towards the pressure liquid infusion unit;
(3) enabling the pressure liquid infusion unit to force the cultivation liquid to flow towards the oxygen discharge and regulation unit so that the cultivation liquid is forced into the oxygen discharge and regulation unit to form a spray of water, whereby the water sprays onto the liquid collection can, and discharging the oxygen; and
(4) collecting the cultivation liquid in the oxygen discharge and regulation unit, and extracting the cultivation liquid to flow into the light permeable piping for further photosynthesis.

In order to further understand the technical means and effects adopted to achieve the objectives of this invention, please refer to the detailed description and accompanied drawings according to this invention. It is believed that the objectives, features, and points of this invention will be apparent from the description; however, the accompanied drawings are provided for reference and illustration only and not intended to limit the terms or scope of this invention.

DETAILED DESCRIPTION OF THE PREFERRED EMBODIMENTS

Figure 1:
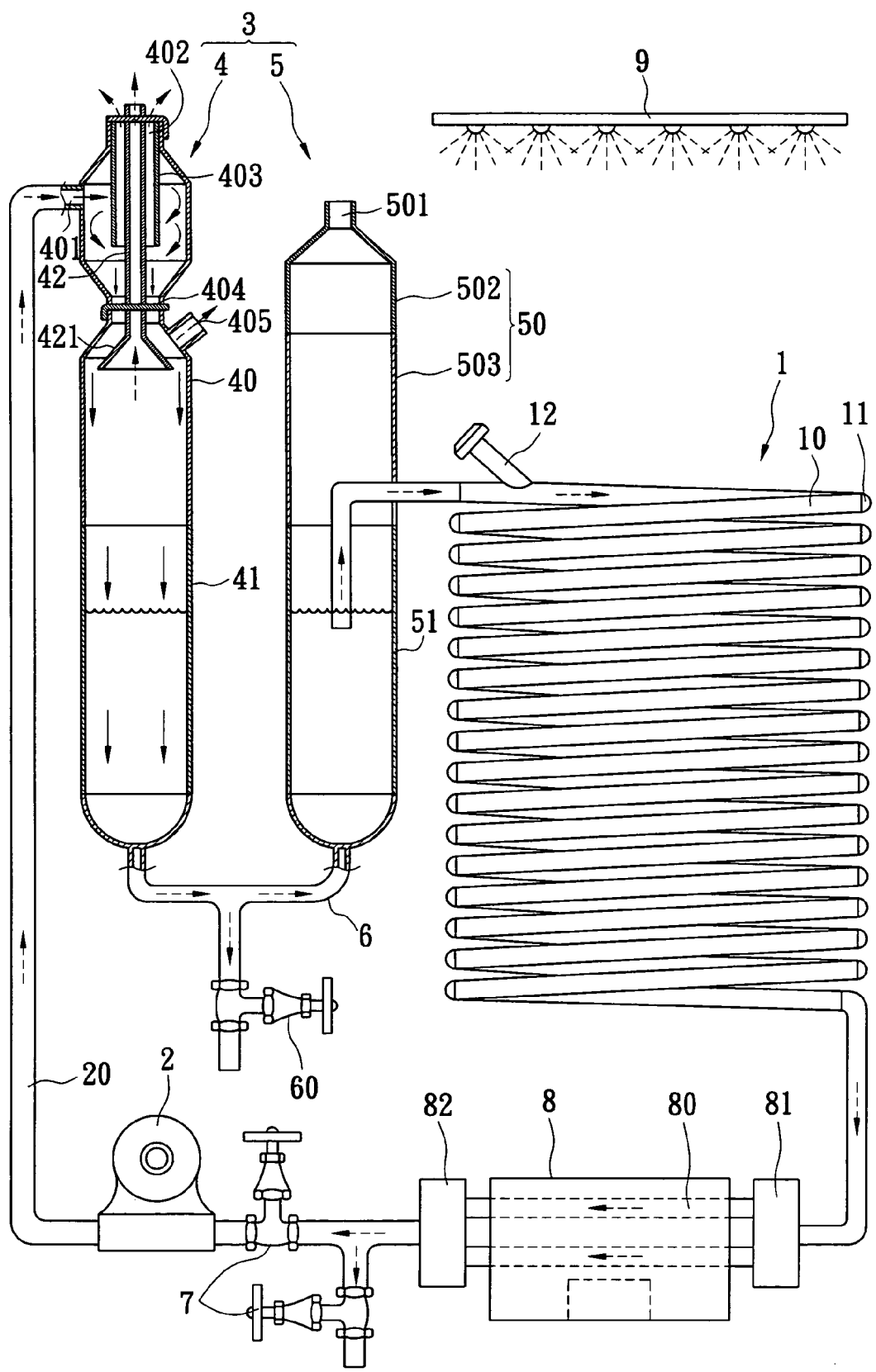
FIG. 1 is a partial sectional view illustrating a vegetable alga and microbe photosynthetic reaction system according to this invention.
Figure 2:
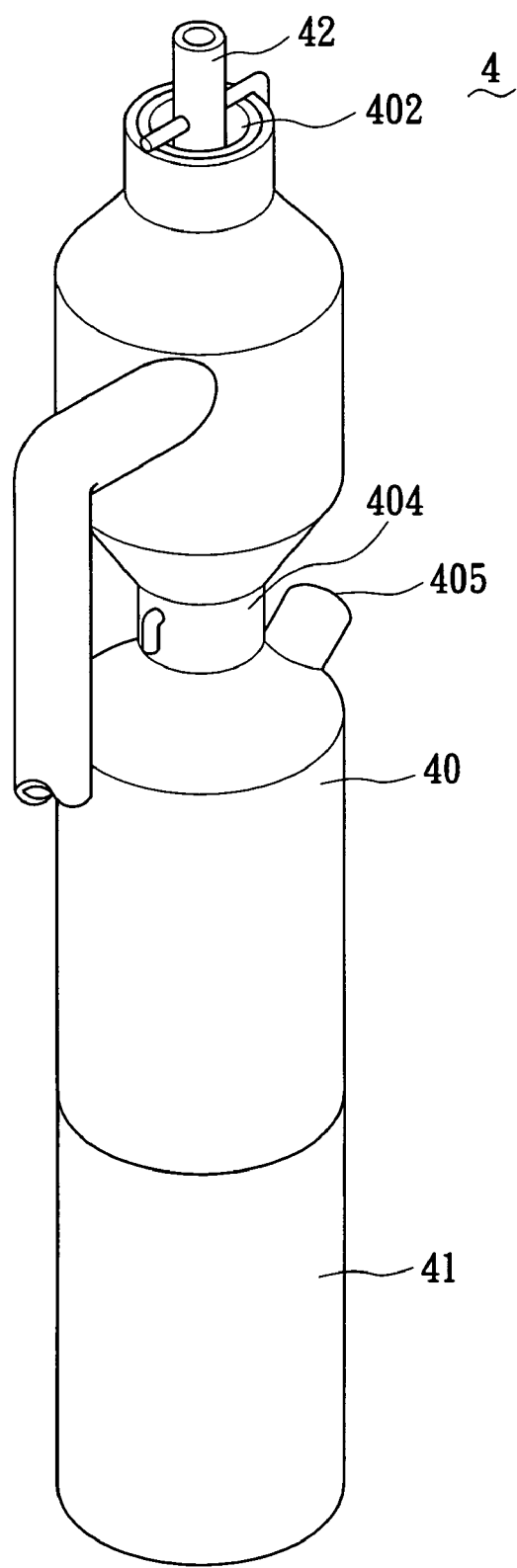
FIG. 2 is a 3D schematic view illustrating an oxygen injection and discharge device of the vegetable alga and microbe photosynthetic reaction system according to this invention.

Referring now to FIGS. 1 and 2, this invention is a vegetable alga and microbe photosynthetic reaction system. Through the system, vegetable algae and microbe cultivation liquid and algae seeds, such as a cultivation liquid for spirulina, infused herein may circularly conduct photosynthesis and discharge oxygen so that spirulina may grow and multiply in large quantities to produce various nutritional ingredients. The vegetable alga and microbe photosynthetic reaction system comprises a photosynthetic reaction unit 1, a pressure liquid infusion unit 2, and an oxygen discharge and regulation unit 3, in which:

The photosynthetic reaction unit 1 is a light permeable pipeline made of a light permeable material of glass or acryl for spirulina cultivation liquid to flow within. In this embodiment, the photosynthetic reaction unit 1 comprises a plurality of straight pipes 10 and a plurality of bent pipes 11. The straight pipes 10 and the bent pipes 11 are serially connected at intervals to form a 3D spiral light permeable pipeline of double rows inclined so that the cultivation liquid flowing therein may flow downwards in a proper sequence and may fully absorb streams of light to generate a photosynthetic reaction. A topmost section of the light permeable pipeline is provided with an auxiliary mouth 12 used to infuse the cultivation liquid and the algae seeds into the pipeline, to regulate pressure inside the light permeable pipeline, and to make cleaning the light permeable pipeline easier.

The pressure liquid infusion unit 2 is a pressure liquid infusion pump in which an entrance is connected to an exit of the light permeable pipeline.

The oxygen discharge and regulation unit 3 comprises a hollow oxygen injection and discharge device 4, a hollow liquid level regulation device 5, and a communicating device 6. The oxygen injection and discharge device 4 comprises an oxygen discharge can 40 and a liquid collection can 41 that are joined to each other. The oxygen discharge can 40 may be made of a stainless steel material while the liquid collection can 41 may be made of a light permeable material such as glass or acryl which facilitates the device's production and assembly, not remaining within the confines of what is required herein. An upper segment of the oxygen discharge can 40 is provided with a liquid entrance 401, a top exhaust 402, and a hollow pipe wall 403, in which the liquid entrance 401 leads to an exit of the pressure liquid infusion unit 2 through an infusion pipe 20, the top exhaust 402 is located at a top of the oxygen discharge can 40, and the hollow pipe wall 403 extends from the top exhaust 402 downwards and is correspondingly located at an inside of the liquid entrance 401. A middle section of the oxygen discharge can 40 is provided with a necking portion 404 and a side exhaust 405, in which the side exhaust 405 is located below the necking portion 404. The oxygen injection and discharge device 4 further comprises an exhaust pipe 42 connected to the oxygen discharge can 40, in which a top end of the exhaust pipe 42 pierces through the hollow pipe wall 403, and a bottom end of the exhaust pipe 42 is formed with a expansion portion 421 and is correspondingly located at an inner side of the side exhaust 405. The liquid level regulation device 5 comprises an extension can 50 and a regulation can 51 that are joined to each other, in which the extension can 50 may be made of a stainless steel material and may be divided into an upper segment 502 and a lower segment 503, thereby the extension can 50 and the regulation can 51 can be easily taken apart for cleaning of the inner walls, and the regulation can 51 may be made of a light permeable material such as glass or acryl for facilitating production and assembly, not remaining within the confines of what is required herein. A top of the extension can 50 is provided with a pressure regulation mouth 501. The communicating device 6 is connected to a bottom of the liquid collection can 41 and a bottom of the regulation can 51, and thereby the regulation can 51 leads to the liquid collection can 41. The communicating device 6 also has a cleaning valve component 60. The entrance of the light permeable pipeline is bent downwards to lead to the regulation can 51.

The vegetable alga and microbe photosynthetic reaction system according to this invention further comprises a picking valve component 7. The picking valve component 7 is connected between the exit of the light permeable pipeline and the entrance of the pressure liquid infusion unit 2 to drain the cultivation liquid from the light permeable pipeline.

When the vegetable alga and microbe photosynthetic reaction system according to this invention is used, the cultivation liquid for spirulina should be infused through the auxiliary mouth 12 to the light permeable pipeline to generate photosynthesis and oxygen. It then flows towards the pressure liquid infusion unit 2. The cultivation liquid may also be infused from the pressure regulation mouth 501 to the regulation can 51. The pressure liquid infusion unit 2 forces the cultivation liquid to flow from the light permeable pipeline to the oxygen discharge and regulation unit 3. When the cultivation liquid is injected into the liquid entrance 401 and then into the oxygen discharge can 40, the cultivation liquid first is forced into the oxygen discharge can 40 and releases a spray of water thereby discharging oxygen out of the top exhaust 402. After falling into the necking portion 404 to be collected, the cultivation liquid is forced into the expansion portion 421 forming a spray of water thereby discharging oxygen out of the side exhaust 405. Finally, the cultivation liquid falls into the liquid collection can 41 and is collected so that the oxygen is discharged out of the exhaust pipe 42. Thus, most of the oxygen is discharged in a way that improves the performance of the process. The oxygen discharge can 40 may be made of a stainless steel material because the cultivation liquid passing through the oxygen discharge can 40 produces a saturated liquid containing oxygen that does not easily conduct photosynthesis. Furthermore, when the cultivation liquid is collected in the liquid collection can 41, most of the oxygen has already been discharged and photosynthesis may occur. As such, the liquid collection can 41 should be made of a light permeable material such as glass. The oxygen discharge can 40 and the liquid collection can 41 are simple to produce and assemble and are not easily damaged. When the cultivation liquid flows through the communicating device 6 to the regulation can 51, the cleaning valve component 60 can be temporarily enabled to cleanse thicker sediments from the liquid. The cultivation liquid may also be sampled for testing. The pressure regulation mouth 501 can also act as an exhaust to reduce pressure in the liquid level regulation device 5. Excessive foam may also be extracted from the liquid level regulation device 5 through the pressure regulation mouth 501. The pressure regulation mouth 501 can further be provided with a supply pipe to supply carbon dioxide to the cultivation liquid as a nutrient to help the alga grow and multiply. Due to the pressure within the pressure liquid infusion unit 2, a negative pressure is generated within the light permeable pipeline so that the cultivation liquid is extracted from the regulation can 51 to the light permeable pipeline for further photosynthesis. If the pressure in the light permeable pipeline increases and makes the cultivation liquid level in the liquid level regulation device 5 rise, the output pressure of the pressure liquid infusion unit 2 may be adjusted to lower the cultivation liquid level. Consequently, the cultivation liquid may circularly conduct photosynthesis and discharge oxygen according to a straight sealed piping of multiple rows for increasing its nutritional ingredients. The cultivation liquid may also be sampled for testing through the picking valve component 7. When a nutrient of the cultivation liquid meets the required concentration, the liquid may be extracted via the picking valve component 7 or the cleaning valve component 60.

The vegetable alga and microbe photosynthetic reaction system according to this invention further comprises a heating unit 8. The heating unit 8 is provided with several heating pipes 80, an entrance forwarding section 81, and an exit forwarding section 82. The heating pipes 80 are connected between the exit of light permeable pipeline and the entrance of the pressure liquid infusion unit 2 respectively through the entrance forwarding section 81 and the exit forwarding section 82. The heating unit 8 can be controlled manually or through an automatic sensor and heats water therein. The heated water delivers heat to the heating pipes 80 to control the temperature of the cultivation liquid. The heating pipes 80 are preferably made of a material, such as stainless steel, that conducts heat well and is durable.

The vegetable alga and microbe photosynthetic reaction system according to this invention further comprises a sprinkling unit 9. The sprinkling unit 9 is located above the photosynthetic reaction unit 1. It can be operated either manually or through an automatic sensor at either a predetermined time or when the environment reaches a predetermined temperature. According to the requirements of the environment, it can lower the temperature of the cultivation liquid in the light permeable pipeline.

Figure 3:
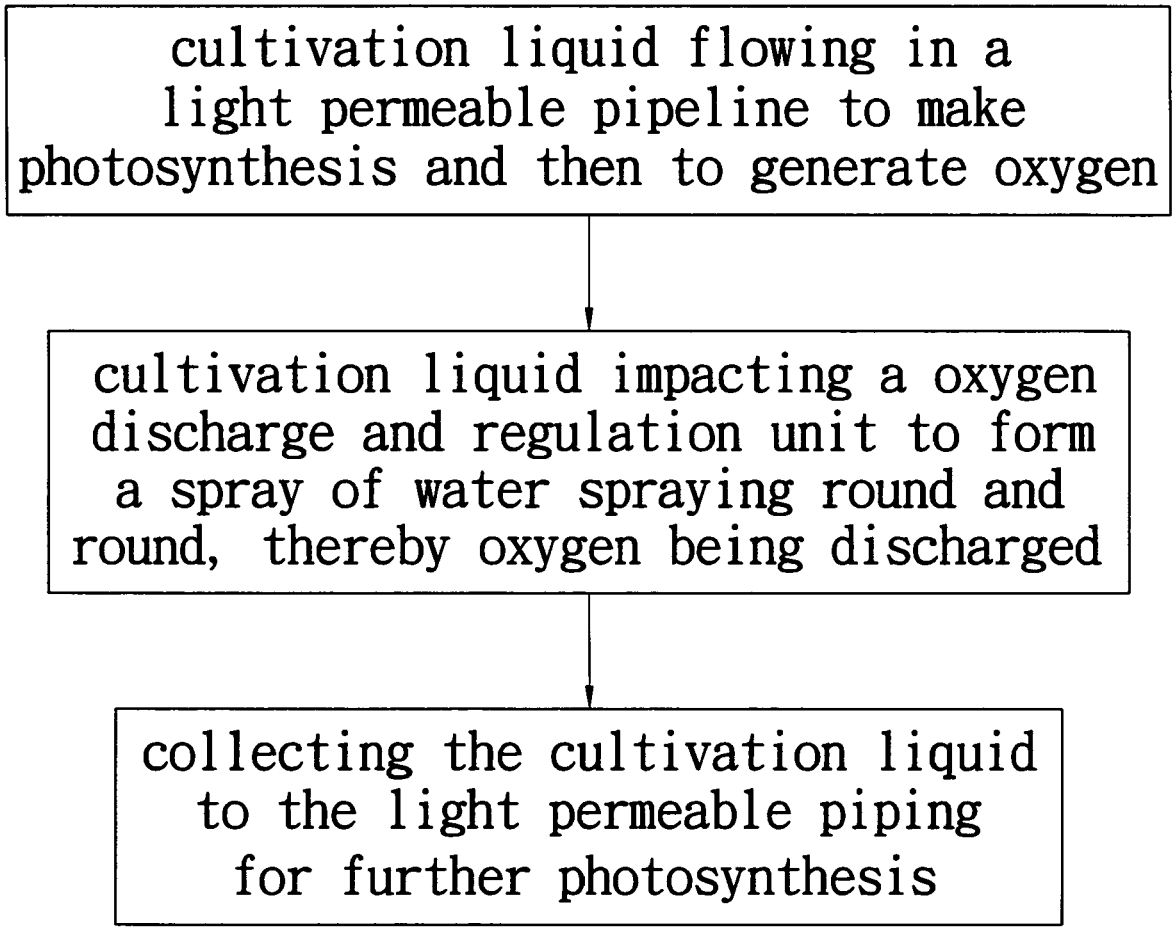
FIG. 3 is a flow chart of a method of the vegetable alga and microbe photosynthetic reaction system according to this invention.

Thus, referring now to FIGS. 1 and 3, this invention provides a method for the vegetable alga and microbe photosynthetic reaction, comprising:

(1) providing a light permeable pipeline, a pressure liquid infusion unit 2, and a oxygen discharge and regulation unit 3: the light permeable pipeline, the pressure liquid infusion unit 2, and the oxygen discharge and regulation unit 3 are connected to form the vegetable alga and microbe photosynthetic reaction system mentioned above;

(2) infusing a cultivation liquid and algae seeds into the light permeable pipeline; the flow of the cultivation liquid through the light permeable pipeline generates photosynthesis and, consequently, oxygen. The cultivation liquid then flows towards the pressure liquid infusion unit 2. The light permeable pipeline is a 3D spiral light permeable pipeline. Thus the cultivation liquid flows to and fro in the light permeable pipeline from top to bottom in sequence so that the cultivation liquid fully absorbs streams of light to generate photosynthesis and promote the rapid growth fast glowing of the alga;

(3) enabling the pressure liquid infusion unit 2 to force the cultivation liquid to flow towards the oxygen discharge and regulation unit 3 so that the cultivation liquid is forced into the oxygen discharge and regulation unit 3 where the cultivation liquid is released as a spray of water, thereby discharging oxygen from the system; and (4) collecting the cultivation liquid within the oxygen discharge and regulation unit 3 and extracting the cultivation liquid so that it flows towards the light permeable pipeline and furthers the photosynthetic process.

Furthermore, at step (1), a heating unit 8 is provided, in which the cultivation liquid flows through the heating unit 8 to the pressure liquid infusion unit 2, thereby controlling the temperature of the cultivation liquid.

At step (2), a sprinkling unit 9 is provided. When necessary, the sprinkling unit 9 waters the light permeable pipeline, thereby lowering the temperature of the cultivation liquid in the light permeable pipeline.

At step (4), a picking valve component 7 is provided. The cultivation liquid, having flowed through the light permeable pipeline and being ready for cultivation, can be extracted via the picking valve component 7.

Accordingly, the vegetable alga and microbe photosynthetic reaction system and method for the same is characterized by:

1. through the connection between the photosynthetic reaction unit, the pressure liquid infusion unit, and the oxygen discharge and regulation unit, the vegetable algae and microbe cultivation liquid and algae seeds infused herein may circularly undergo photosynthesis, discharging oxygen through a straight sealed pipe of multiple rows. Thus the system occupies less area, consumes less power, works unaffected by the weather, and prevents pollution from affecting the quality of the alga;
2. through the arrangement of the liquid entrance, the top exhaust, the hollow pipe wall, the arrangement of the exhaust pipe, the necking portion, and the side exhaust, oxygen may be discharged at many different times. As such, any oxygen formed within the cultivation liquid is quickly evaporated out thus promoting production efficiency and aiding in the mass production of the alga;
3. through the assembly of the oxygen discharge can and the liquid collection can into the hollow oxygen injection and discharge device, and the assembly of the regulation can and the extension can into the liquid level regulation device, the production and assembly procedures are simple and the system is not easily damaged, thereby lowering production costs;
4. through the assembly of the oxygen discharge can and the liquid collection can, and the design of the light permeable pipeline, cleaning and maintenance of the structure are simple, thus ensuring the photosynthetic reaction takes place effectively and that the alga produced is of a high quality; and
5. through the arrangement of the heating unit and the sprinkling unit, the temperature of the cultivation liquid may be efficiently controlled irrespective of the area, season, weather or other factors that may otherwise affect the production process.

To sum up, this invention completely meets the requirements of an application for protection under patent law. We earnestly request that this application be examined in detail and approved as soon as possible for protection of the inventor's rights and interests. Please feel free to contact us if you, the examiner, have any questions at the time of examination.

However, the detailed description and drawings of the embodiments according to this invention are provided without the intention of limiting its scope or characteristics. Those of ordinary skill in the art should include any equivalent changes and modifications as falling within the true scope and spirit of the present invention.

What is claimed is:

1. A vegetable alga and microbe photosynthetic reaction system, comprising:
    a photosynthetic reaction unit serving as a light permeable pipeline;
    a pressure liquid infusion unit in which an entrance leads to an outlet of the light permeable pipeline; and
    an oxygen discharge and regulation unit comprising a hollow oxygen injection and discharge device and a hollow liquid level regulation device, in which the oxygen injection and discharge device comprises an oxygen discharge can and a liquid collection can that are joined to each other, the oxygen discharge can is provided with a liquid entrance, a top exhaust, and a hollow pipe wall, the liquid entrance leads to an exit of the pressure liquid infusion unit, the top exhaust is located at a top of the oxygen discharge can, the hollow pipe wall extends from the top exhaust downwards and is correspondingly located at an inside of the liquid entrance, the liquid level regulation device comprises a regulation can leading to the liquid collection can, and an entrance of the light permeable pipeline leads to the regulation can.

2. The vegetable alga and microbe photosynthetic reaction system according to claim 1, wherein the photosynthetic reaction unit comprises a plurality of straight pipes and a plurality of bent pipes and the straight pipes and the bent pipes are serially connected at intervals to form an inclined 3D spiral light permeable pipeline of double rows.

3. The vegetable alga and microbe photosynthetic reaction system according to claim 1, wherein a topmost section of the light permeable pipeline is provided with an auxiliary mouth.

4. The vegetable alga and microbe photosynthetic reaction system according to claim 1, wherein the pressure liquid infusion unit is a pressure liquid infusion pump.

5. The vegetable alga and microbe photosynthetic reaction system according to claim 1, wherein the oxygen injection and discharge device comprises an exhaust pipe connected to the oxygen discharge can, a middle section of the oxygen discharge can is provided with a necking portion and a side exhaust, the side exhaust is located below the necking portion, a top end of the exhaust pipe pierces through the hollow pipe wall, and a bottom end of the exhaust pipe is formed with an expansion portion and is correspondingly located at an inner side of the side exhaust.

6. The vegetable alga and microbe photosynthetic reaction system according to claim 1, wherein the liquid level regulation device comprises an extension can and the regulation can that are joined to each other, and the extension can is provided with a pressure regulation mouth.

7. The vegetable alga and microbe photosynthetic reaction system according to claim 1, wherein the oxygen discharge and regulation unit comprises a communicating device connected to a bottom of the liquid collection can and a bottom of the regulation can and provided with a cleaning valve component.

8. The vegetable alga and microbe photosynthetic reaction system according to claim 1, further comprising a picking valve component connected between the exit of the light permeable pipeline and the entrance of the pressure liquid infusion unit.

9. The vegetable alga and microbe photosynthetic reaction system according to claim 1, further comprising a heating unit connected between the exit of the light permeable pipeline and the entrance of the pressure liquid infusion unit.

10. The vegetable alga and microbe photosynthetic reaction system according to claim 1, further comprising a sprinkling unit located above the photosynthetic reaction unit.

11. A vegetable alga and microbe photosynthetic reaction method, comprising:
    (1) providing a light permeable pipeline, a heating unit, a pressure liquid infusion unit, and an oxygen discharge and regulation unit;

(2) injecting a cultivation liquid and algae seeds into the light permeable pipeline, the cultivation liquid flowing in the light permeable pipeline to make photosynthesis and then to generate oxygen, and also flowing through the heating unit towards the pressure liquid infusion unit;

(3) enabling the pressure liquid infusion unit to force the cultivation liquid to flow towards the oxygen discharge and regulation unit so that the cultivation liquid impacts the oxygen discharge and regulation unit to form a spray of water spraying round and round, thereby oxygen being discharged; and (4) collecting the cultivation liquid in the oxygen discharge and regulation unit, and extracting the cultivation liquid to flow into the light permeable piping for further photosynthesis.

12. The vegetable alga and microbe photosynthetic reaction method according to claim 11, wherein at step (2) the cultivation liquid flows to and fro in the light permeable pipeline from top to bottom in sequence.

13. A vegetable alga and microbe photosynthetic reaction method, comprising:

(1) providing a light permeable pipeline, a pressure liquid infusion unit, and an oxygen discharge and regulation unit;

(2) providing a sprinkling unit that waters the light permeable pipeline and injecting a cultivation liquid and algae seeds into the light permeable pipeline, the cultivation liquid flowing in the light permeable pipeline to make photosynthesis and then to generate oxygen, and also flowing through the heating unit towards the pressure liquid infusion unit;

(3) enabling the pressure liquid infusion unit to force the cultivation liquid to flow towards the oxygen discharge and regulation unit so that the cultivation liquid impacts the oxygen discharge and regulation unit to form a spray of water spraying round and round, thereby oxygen being discharged; and (4) collecting the cultivation liquid in the oxygen discharge and regulation unit, and extracting the cultivation liquid to flow into the light permeable piping for further photosynthesis.

14. The vegetable alga and microbe photosynthetic reaction method according to claim 11, wherein at step (4) a picking valve component is provided and the cultivation liquid, after flowing through the light permeable pipeline, is extracted by the picking valve component.

* * * * *